United States Patent [19]

Doenges et al.

[11] Patent Number: 4,966,828
[45] Date of Patent: Oct. 30, 1990

[54] CARBONYLMETHYLENE-HETEROCYCLIC COMPOUNDS CONTAINING TRIHALOGENOMETHYL GROUPS, PROCESS FOR THEIR PREPARATION, AND LIGHT-SENSITIVE MIXTURE CONTAINING THE COMPOUNDS

[75] Inventors: Reinhard Doenges, Bad Soden; Hans Ruckert, Wiesbaden-Naurod; Ulrich Geissler, Frankfurt am Main; Hartmut Steppan, Wiesbaden-Dotzheim, all of Fed. Rep. of Germany

[73] Assignee: Hoechst Aktiengesellschaft, Frankfurt, Fed. Rep. of Germany

[21] Appl. No.: 651,116

[22] Filed: Sep. 13, 1984

[30] Foreign Application Priority Data

Sep. 16, 1983 [DE] Fed. Rep. of Germany ....... 3333450

[51] Int. Cl.$^5$ ............... G03C 1/675; G03F 7/028; G03F 7/038; C07D 209/04
[52] U.S. Cl. ............................. 430/281; 430/922; 430/270; 430/280; 430/343; 430/292; 522/34; 522/45; 548/491; 548/217; 548/150; 548/148; 548/180; 548/147; 548/120; 548/121; 546/174
[58] Field of Search ............... 548/491, 217, 150, 148, 548/180, 147, 120, 121; 546/174; 430/281, 922; 204/159.23, 159.22; 130/270, 280, 343, 292; 522/34, 45

[56] References Cited

U.S. PATENT DOCUMENTS

| | | | |
|---|---|---|---|
| T900,011 | 12/1969 | Bloom et al. | 430/270 |
| 2,505,067 | 4/1950 | Sachs et al. | 522/67 |
| 2,548,685 | 4/1951 | Sachs et al. | 522/45 |
| 2,641,576 | 6/1953 | Sachs et al. | 522/45 |
| 2,732,301 | 1/1956 | Robertson et al. | 96/115 R |
| 3,030,208 | 4/1962 | Schellenberg et al. | 430/285 |
| 3,453,237 | 7/1969 | Borden et al. | 430/285 |
| 3,827,957 | 8/1974 | McGinisse | 430/923 X |
| 3,870,524 | 3/1975 | Watanabe et al. | 430/923 X |
| 4,033,952 | 7/1977 | Tieman | 260/243 R |
| 4,040,922 | 9/1977 | Wang et al. | 522/45 |
| 4,058,398 | 11/1977 | Osada et al. | 430/920 |
| 4,111,692 | 9/1978 | Etoh et al. | 522/45 X |
| 4,119,466 | 10/1978 | Van Allan et al. | 430/286 |
| 4,189,323 | 2/1980 | Buhr | 430/281 |
| 4,232,106 | 11/1980 | Iwasaki et al. | 430/170 |
| 4,239,850 | 12/1980 | Kita et al. | 430/285 X |
| 4,371,606 | 2/1983 | Doenges | 430/281 |
| 4,371,607 | 2/1983 | Doenges | 430/281 |

FOREIGN PATENT DOCUMENTS

| | | |
|---|---|---|
| 0135348 | 3/1985 | European Pat. Off. . |
| 466269 | 5/1937 | United Kingdom ................ 548/121 |
| 1388492 | 3/1975 | United Kingdom . |
| 1584741 | 2/1981 | United Kingdom . |

OTHER PUBLICATIONS

Antonia Cipiciani, et al., "The Mechanism of Trifluoroacetylation of Indoles", Journal of the Chemical Society, (1982).
A. Bailey et al., "The Reactions of 1,2,3-Trimethylindole ... Anhydride", Journal of the Chemical Society, 1981.
A. Bailey et al., "Reactions of Some Heterocyclic ... Anhydride", Journal of the Chemical Society, (1983).
Jaromir Kosar, "Light-Sensitive Systems:", Chemistry and Application of Nonsilver Halide Photographic Processes, pg. 145-151, 1965.
Chiaka, E. A. et al. "Carbocyanine Dyes with Chlorine Atoms and Trichloromethyl Groups in the Chain", Zhurnal Organicheskoi Khimii,, vol. 18, No. 1, pp. 186-193, Jan. 1982, translated to English in *Journal of Organic Chemistry of the U.S.S.R., vol. 18, 1983, pp. 165-171*.
Jerry March, "Chapter 1; Electronegativity", *Advanced Organic Chemistry: Reactions, Mechanisms and Structure*, 2nd edition, McGraw-Hill, Inc., New York, N.Y., 1977, pp. 17-20.

Primary Examiner—Cynthia Hamilton
Attorney, Agent, or Firm—Foley & Lardner, Schwartz, Jeffery, Schwaab, Mack, Blumenthal & Evans

[57] ABSTRACT

Disclosed is a compound of the general formula

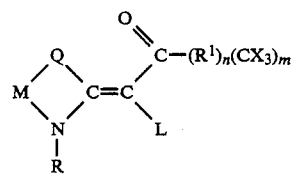

wherein L=H or CO—$(R^1)_n(CX_3)_m$, M=alkylene, alkenylene, Q=S, Se, O, dialkylmethylene, alken-1,2-ylene, 1,2-phenylene or N-R, with M+Q together forming 3 or 4 ring members, R=alkyl, aralkyl or alkoxyalkyl, $R^1$ is an aromatic group and X=Cl, Br or I, with n=0 and m=1 or n=1 and m=1 or 2. The compounds, on exposure, eliminate HX and form free radicals and are therefore highly effective as acid donors and free radical initiators for photochemical processes.

13 Claims, No Drawings

CARBONYLMETHYLENE-HETEROCYCLIC COMPOUNDS CONTAINING TRIHALOGENOMETHYL GROUPS, PROCESS FOR THEIR PREPARATION, AND LIGHT-SENSITIVE MIXTURE CONTAINING THE COMPOUNDS

BACKGROUND OF THE INVENTION

The present invention relates to 1-alkyl-2-carbonyl-methylene-heterocyclic compounds having at least one trichloromethyl group on the substituent in the 2-position, to a process for their preparation and to a light-sensitive mixture containing these compounds.

It is known to employ heterocyclic compounds containing trichloromethyl groups as initiators for various photochemical reactions.

German Offenlegungsschrift No. 2,243,621 discloses s-triazines which are substituted by one or two trichloromethyl groups and one chromophoric group and are suitable as photoinitiators in photopolymerisable mixtures and as acid donors in a mixture with acetals which can be split by acid.

Similar compounds, in which an at least binuclear aromatic radical as a chromophoric group is bonded directly to the triazine ring, are disclosed in German Offenlegungsschrift No. 2,718,259 (=U.S. Pat. No. 4,189,323).

German Offenlegungsschrift No. 2,851,472 describes light-sensitive mixtures which contain 2-halogenomethyl-5-vinyl-1,3,4-oxadiazole derivatives as photoinitiators.

German Offenlegungsschriften Nos. 3,021,590 and 3,021,599 disclose halogenoxazoles which are substituted by trichloromethylphenyl groups and are suitable as photoinitiators, like the above-mentioned compounds.

Moreover, light-sensitive mixtures which are based on unsaturated compounds or polymeric azides and which, as sensitizers, contain 2-heteroyl-carbonyl-methylene-benzothiazoles or -benzoselenazoles, are described in German Auslegeschrift No. 2,717,778.

The known photoinitiators have the following disadvantages:

The reaction conditions for preparing the compounds are fairly drastic so that the yield is relatively low and the formation of undesired by-products is favored (for example, German Offenlegungsschriften Nos. 2,243,621, 2,718,259, or 2,851,472), or the use of certain catalysts permits the presence of only a few defined functional groups in the molecule (for example, German Offenlegungsschrift No. 2,718,259).

With many know initiators, the inadequate sensitivity makes it necessary to combine different initiator systems with one another.

It has proven to be a particular disadvantage that precisely the most sensitive of the known initiators do not have a storage stability which meets the requirements in practice in light-sensitive mixtures, in particular in contact with copper surfaces.

SUMMARY OF THE INVENTION

It is, therefore, an object of the present invention to provide a novel light-sensitive compound which can be used in various light-sensitive materials.

Another object of the present invention is the provision of a light-sensitive compound which is readily accessible and offers a wide range of possible variations, thus being adaptable in an optimum manner to the requirements of each of the various fields of application. For example, the compound should have a wide spectral sensitivity range, i.e. the compound should be sensitive especially in the near ultraviolet and short-wave visible range of light. In addition, when used in light-sensitive mixtures for reprography, for example in printing plates, the compound should show a clearly visible image contrast in the light-sensitive layer immediately after irradiation.

Yet another object of the present invention is the provision of light-sensitive mixtures containing the novel initiators having a high storage stability, irrespective of the material of the support on which the mixtures are present.

Still another object of the present invention is to provide a process for preparing the light-sensitive compounds described above.

Therefore, in accordance with one aspect of the present invention, there has been provided a compound of the general formula I

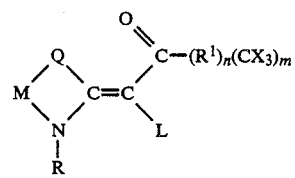

wherein:
L represents a hydrogen atom or a substituent of the formula $CO\text{-}(R^1)_n(CX_3)_{m'}$
M represents a substituted or unsubstituted alkylene radical or alkenylene radical or a 1,2-arylene radical,
Q represents a sulfur, selenium or oxygen atom, a dialkylmethylene group, an alken-1,2-ylene radical, a 1,2-phenylene radical or an N-R group, whereby M+Q together form 3 or 4 ring members,
R represents an alkyl, aralkyl or alkoxyalkyl radical,
$R^1$ represents a carbocyclic or heterocyclic aromatic group, and
X represents a chlorine, bromine or iodine atom, with
$n=0$ and $m=1$, or
$n=1$ and $m=1$ or 2.

In accordance with another aspect of the present invention, there has been provided a light-sensitive mixture which comprises a light-sensitive heterocyclic organic compound (a) of formula I mentioned above, which has at least one trihalogenomethyl substituent and a compound (b) which is capable of reacting with the photoreaction product of the organic compound (a) to form a product having a light absorption or solubility in a developer which differs from that of compound (b).

In accordance with yet another aspect of the present invention, there has been provided a process for preparing a compound of the formula I, comprising the steps of reacting a compound of the formula II

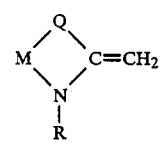

(II)

or an iminium salt thereof, of the formula III

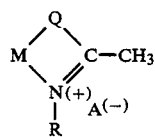

wherein $A^{(-)}$ represents the anion of the iminium salt, with a carboxylic acid halide of the formula IV

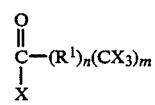

wherein L, M, Q, R, $R^1$, X, n and m are defined as above.

Other objects, features and advantages of the present invention will become apparent from the detailed description of preferred embodiments which follows.

DETAILED DESCRIPTION OF PREFERRED EMBODIMENTS

The object of the present invention is achieved by compounds of the general formula I

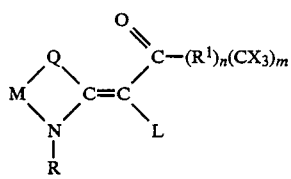

in which

L is a hydrogen atom or a substituent of the formula $CO\text{-}(R^1)_n(CX_3)_{m'}$ M is a substituted or unsubstituted alkylene radical or alkenylene radical or a 1,2-arylene radical, Q is a sulfur, selenium or oxygen atom, a dialkylmethylene group, an alken-1,2-ylene radical, a 1,2-phenylene radical or an N-R group, M+Q together forming 3 or 4 ring members, R is an alkyl, aralkyl or alkoxyalkyl radical, $R^1$ is a carbocyclic or heterocyclic aromatic group and X is a chlorine, bromine or iodine atom, with n=0 and m=1 or
n=1 and m=1 or 2.

According to the invention, a light-sensitive mixture is also proposed, which comprises a light-sensitive heterocyclic organic compound (a) with at least one trihalogenomethyl substituent and a compound (b) which is capable of reacting with the photoreaction product of the organic compound (a) with the formation of a product, of which the light absorption or solubility in a developer differs from that of (b). The mixture according to the invention comprises a compound (a) which is a compound of the formula I given above.

Under the action of actinic radiation, the compounds according to the present invention form free radicals which are capable of initiating chemical reactions, in particular polymerizations initiated by free radicals. On irradiation, the compounds also release hydrogen halide, by means of which acid-catalyzed reactions, for example the cleavage of acetal bonds, or formation of salts, for example color changes of indicator dyes, can be set in motion.

In the formula I, L is preferably a hydrogen atom. M is preferably a 1,2-phenylene radical which is preferably unsubstituted, but can be substituted, for example, by halogen atoms or carboxyl, sulfonic acid, nitro, cyano, carbonyl, alkyl, aryl, alkoxy, trifluoromethyl or alkoxycarbonylalkyl groups. M can also be a heterocyclic aromatic radical, for example, a pyridylene radical. When M is a polynuclear aryl radical, it can contain 2 or 3, but preferably 2 benzene nuclei. M can also be a 1,2- or 1,3-alkenylene radical which can be substituted, for example by halogen atoms or carboxyl, carbonyl, alkoxy, alkyl or aryl groups. Moreover, M can be a 1,1-, 1,2- or 1,3-alkylene radical which may also carry substituents of the same type.

Q is preferably a sulfur atom, an NR group or a dialkylmethylene group having about 3 to 13, preferably about 3 to 7 and especially 3 carbon atoms. Q can also be an oxygen or selenium atom, a 1,2-alkenyl group, a 1,2-phenylene group or a carbonyl or thiocarbonyl group. If Q is a dialkylmethylene group, the alkyl groups can be linked to one another with the formation of a 5-membered or a 6-membered ring. If Q is a 1,2-alkenylene group, Q can be substituted, among other ways, by one or two alkyl or phenyl radicals, chlorine atoms, alkoxy groups or alkoxycarbonyl groups. If Q is a 1,2-phenylene radical, Q can contain, for example, chlorine atoms or alkoxy or alkoxy carbonyl groups as substituents. Preferably, Q is S, in particular as a constituent of a 5-membered ring.

When R is an alkyl or alkoxyalkyl radical, R can, in general, comprise about 1-10, preferably about 1-6 carbon atoms. The radical can be straight-chain or branched, or it can be cyclized to give a cycloaliphatic radical, for example, a cyclohexyl radical. Examples of aralkyl radicals include benzyl, chlorobenzyl, tolylmethyl and phenethyl radicals. Preferably, R is an alkyl radical having about 1-3 carbon atoms. $R^1$ is a mononuclear or binuclear aromatic group, preferably a mononuclear aromatic group, which is preferably carbocyclic. Examples of $R^1$ include benzene, naphthalene, triazole, pyrimidine, pyridine, oxazole, imidazole, thiazole, oxadiazole, thiadiazole, furan, thiophene, pyrrole and isoxazole rings which can be substituted by halogen atoms, alkoxy groups or alkyl groups.

X is preferably a chlorine or bromine atom, in particular a chlorine atom. In general, compounds with n=1 are preferred.

The compounds according to the present invention can advantageously be prepared analogously to known processes [for example, A Mistr, V. Laznicka and M. Vavra, Coll. Czech. Chem. Commun. 36, 150 (1971)] from a methylene compound of the formula II or the corresponding iminium salt of the formula III and a carboxylic acid halide of the formula IV:

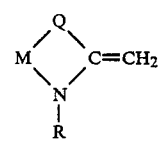

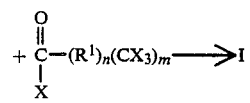

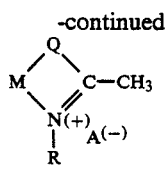

(III)

in which A is an inorganic anion, preferably a halide anion, tetrafluoborate anion or perchlorate anion, or an organic anion, preferably a sulfonate anion or alkylsulfate anion, and the remaining symbols are as defined above.

The reaction preferably takes place under the action of nitrogen bases, for example, triethylamine, dimethylbenzylamine, diethylbenzylamine, N-ethyldicyclohexylamine, N-ethylpiperidine, N-methylpiperidine, N-methylmorpholine, N-ethylmorpholine, N-ethylpyrrolidone, 1,8-diaza-bicyclo-[5,4,0] undec-7-ene, 1,4-diaza-bycyclo[2,2,2] octane or pyridine, the base itself being used as the solvent or an inert organic solvent being added. The solvents added include, for example, benzene, toluene, dimethylformamide, tetrahydrofuran, diethyl ether, diisopropyl ether and methylene chloride. The reaction is advantageously carried out at temperatures between about 0° and 100° C., the quantity of the carboxylic acid halide generally being between about 1 and 4, preferably between about 1 and 1.5 moles per mole of II or III, for the preparation of products with L=H, and between about 2 and 3 moles per mole of II or III for the preparation of products with $L=CO(R^1)_n(CX_3)_m$.

The compounds according to the invention are suitable as photoinitiators for photopolymerizable layers which contain monomers, binders and initiators as the essential constituents.

Photopolymerizable monomers which can be used in this application are known and are described, for example, in U.S. Pat. Nos. 2,760,863 and 3,030,023.

The acrylates and methacrylates of polyhydric alcohols including diglycerol diacrylate and polyethylene glycol dimethacrylate, and acrylates and methacrylates of trimethylolethane, trimethylolpropane, pentaerythritol and polyhydric alicyclic alcohols are preferred.

Also preferred are reaction products of the diisocyanates with partial esters of polyhydric alcohols. Monomers of this type are described in German Offenlegungsschriften No. 2,064,079; No. 2,361,041 and No. 2,822,190.

The quantitative proportion of monomers in the layer is, in general, about 10 to 80% by weight, preferably about 20 to 60% by weight.

A large number of soluble organic polymers can be employed as binders. Exemplary binders include polyamides, polyvinyl esters, polyvinyl acetals, polyvinyl ethers, epoxide resins, polyacrylates, polymethacrylates, polyesters, alkyd resins, polyacrylamides, polyvinyl alcohol, polyethylene oxide, polydimethylacrylamide, polyvinylpyrrolidone, polyvinylmethylformamide, polyvinylmethyl-acetamide and copolymers of the monomers forming the homopolymers listed.

Further binders include natural materials or processed natural materials, for example gelatine and cellulose ethers.

Advantageously, those binders are used which are water-insoluble but are soluble or at least swellable in aqueous-alkaline solutions, since layers with such binders can be developed with the preferred aqueous-alkaline developers. Binders of this type can, for example, contain the following groups: —COOH, —PO$_3$H$_2$, —SO$_3$H, —SO$_2$NH—, —SO$_2$NHSO$_2$—and —SO$_2$N-H—CO—.

The following may be mentioned as examples of these: maleate resins, polymers of β-methacryloyloxyethyl N-(p-tolylsulfonyl)-carbamate and copolymers of these and similar monomers with other monomers as well as styrene/maleic anhydride copolymers. Alkyl methacrylate/methacrylic acid copolymers and copolymers of methacrylic acid, alkyl methacrylates and methyl methacrylate and/or styrene, acrylonitrile and others, as described in German Offenlegungsschriften No. 2,064,080 and No. 2,363,806, are preferred.

The quantity of binder comprises, in general, about 20 to 90% by weight, preferably about 40 to 80% by weight, of the constituents of the layer.

Depending on the intended use and depending on the desired properties, the photopolymerisable mixtures include various substances as additives. Examples include: inhibitors for preventing thermal polymerization of the monomers, hydrogen donors, substances which modify the sensitometric properties of such layers, dyes, colored and colorless pigments, color formers, indicators, plasticizers, and the like.

The photopolymerizable mixture can be used for the most diverse applications, for example, for the procured by light or corpuscular radiation, for example electron beams, in the dental field and especially as a light-sensitive copying material in the reproduction field. The following may be mentioned as possible applications in this field: copying layers for the photomechanical production of printing forms for letterpress printing, planographic printing, gravure printing and screen printing or relief copies, for example, for the preparation of texts in Braille, of single copies, tanned images, pigment images and the like. Moreover, the mixtures can be used for the photomechanical production of etch resists, for example, for making name tags copied circuits and for chemical milling.

The commercial utilization of the mixture for the applications mentioned can take place in the form of a liquid solution or dispersion, for example, as a photoresist solution, which is applied by the user himself to an individual support, for example, for chemical milling and for the production of printed circuits, screen-printing stencils and the like. The mixture can also be present as a solid light-sensitive layer on a suitable support in the form of a light-sensitive copying material, which has been precoated for storage stability, for example, for the preparation of printing forms. It is likewise suitable for the preparation of dry resists.

In general, it is advantageous to protect the mixtures from the influence of atmospheric oxygen during the photopolymerization. When the mixture is used in the form of thin copying layers, it is advisable to apply a suitable covering film having low oxygen permeability. This film can be self-supporting and can be peeled off before the copying layer is developed. For example, polyester films are suitable for this purpose. The covering film can also comprise a material which is soluble in the developer fluid or can at least be removed from the unhardened areas during developing. Examples of materials suitable for this purposes are waxes, polyvinyl alcohol, polyphosphates, sugars and the like.

Examples of suitable supports for the copying materials, produced with the mixture according to the present invention, are aluminum, steel, zinc, copper and plastic films, for example, of polyethylene terephthalate of cellulose acetate, and screen-printing supports such as gauze polyamide 6.

the radiation-sensitive compounds are effective as photoinitiators even in concentrations of about 0.1% of total solids in the mass, and an increase to more than about 15% is, in general, inappropriate. Preferably, concentrations of about 0.2 to 5% are used.

Moreover, the compounds according to the invention can also be used in those radiation-sensitive mixtures in which a change in properties is initiated by acid catalysts formed during the photolysis of the initiator. For instance, the cationic polymerization of systems which contain vinyl ethers, N-vinyl compounds, such as N-vinylcarbazole, or special acid-cleavable lactones, may be mentioned here, whereby free-radical processes can also participate in some of these reactions. Further acid-curable compositions include aminoplasts, such as urea/formaldehyde resins, melamine/formaldehyde resins and other n-methylol compounds as well as phenol/formaldehyde resins. Even though the hardening of epoxy resins generally takes place by means of Lewis acids or acids, the anions of which are less nucleophilic than chloride and bromide, that is to say the anions of the hydrohalic acids which are formed during the photolysis of the novel compounds, layers which comprise epoxy resins and novolaks are, nevertheless, fully cured on exposure to light in the presence of the compounds according to the invention.

A further advantageous property of the novel compounds is their ability to cause color changes in dyed systems during photolysis, namely to induce color formation from color precursors, for example, leuco compounds, or to effect bathochromic color shifts and deepening in mixtures which contain cyanine, merocyanine or styryl dye bases. Moreover, for example, in the mixtures described in German Offenlegungsschrift No. 1,572,080, which contain a dye base, N-vinylcarbazole and a halogenohydrocarbon, the halogen compound tetrabromomethane can be replaced by a compound according to the present invention in a quantity which is a fraction of the quantity of the former. Color changes are also desired in industry, for example, in the production of printing forms, so that the result of copying can be assessed after exposure even before developing.

The present compounds can be used advantageously in place of the acid donors mentioned in German Offenlegungsschriften Nos. 2,331,377 and 2,641,100.

A particularly preferred field of application for the compounds according to the invention is in mixtures which, in addition to the latter, contain a compound with at least one C—O—C grouping, which can be split by acid, as an essential component. The following may be mentioned as preferred compounds which can be split by acid:

(A) those having at least one orthocarboxylate and/or carboxamide acetal grouping, it also being possible for the compounds to have a polymeric character and for the groupings to be present as linking elements in the main chain or as lateral substituents, and (B) polymer compounds with recurring acetal and/or ketal groupings.

Type A compounds, which can be split by acid, as components of radiation-sensitive mixtures are described extensively in German Offenlegungsschrift Nos. 2,610,842 or 2,928,636; mixtures containing Type B compounds are the subject of the German Pat. No. 2,718,254.

As compounds which can be split by acid, the aryl alkyl acetals and aminals of German Pat. No. 2,306,248, which are likewise degraded by the photolysis products of the compounds according to the present invention, may also be mentioned as examples.

Those mixtures in which molecules are converted into smaller molecules directly or indirectly by the action of actinic radiation have, in general, an increased solubility, tackiness or volatility in the irradiated areas. These portions can be removed by suitable measures, for example by dissolution with a developer fluid. In copying materials these cases are called positively-working systems.

The novolak condensation resins, proven in many positive copying materials, have also proved to be particularly useful and advantageous as additives when the compounds according to the invention are used in mixtures with compounds which can be split by acid. The resins promote the strong differentiation between the exposed and unexposed layer portions on developing, in particular the more highly condensed resins with substituted phenols as the formaldehyde condensation partner. The nature and quantity of the novolak resins can vary depending on the intended purpose; novolak fractions between about 30 and 90% by weight, particularly between about 55–85% by weight, based on total solids content, are preferred.

In addition, numerous other resins can also be included, preferably vinyl polymers, such as polyvinyl acetates, polyacrylates, polyvinyl ethers and polyvinylpyrrolidones, which in turn can have been modified by comonomers. The most advantageous proportion of these resins depends on the requirements in the particular application and the influence on the developing conditions. In general, the proportion in not more than about 20% of the novolak. For special requirements, such as flexibility, adhesion and glass and the like, the light-sensitive mixture can also contain small quantities of substances such as polyglycols, cellulose derivatives such as ethylcellulose, wetting agents, dyes and finely divided pigments as well as ultraviolet absorbers, when required. Developing is preferably carried out with the aqueous-alkaline developers which are common in industry and which can also contain small proportions of organic solvents, or with organic solvents.

The supports already listed in connection with the photopolymerizable mixtures can also be used for positive-working copying materials, further suitable supports are the silicon and silica surfaces conventional in microelectronics.

The quantity of the compounds according to the invention, used as the photoinitiator, in the positive-working mixtures can vary widely depending on the substance and layer. Fairly advantageous results are obtained with quantities between about 0.1 and 10%, preferably between about 0.2 to 5%, relative to total solids. For layers greater than about 10 μm thickness, it is advisable to use relatively small quantities of acid donor.

Electromagnetic radiation of wavelengths of up to about 600 nm is in principle suitable for exposure. The preferred wavelength range extends from about 250 to 500 nm.

The wide variety of the compounds according to the invention, the absorption maxima of which are to be found in some cases even far into the visible part of the spectrum and the absorption range of which can extend beyond 500 nm, makes it possible to match the photoinitiator in an optimum manner to the light source used. As examples of light sources, the following may be mentioned: fluorescent tubes, pulsed xenon lamps, metal halide-doped mercury vapor high-pressure lamps and carbon arc lamps.

Moreover, with the light-sensitive mixtures according to the present invention, exposure in conventional projection and enlargement apparatus under the light of the metal filament lamps and contact exposure with ordinary incandescent bulbs are possible. The exposure can also be made with the coherent light of a laser. Short-wave lasers of appropriate power, for example, argon lasers, krypton ion lasers, dye lasers and helium/-cadmium lasers which emit, in particular, between about 250 and 500 nm, are suitable for the purposes of the present invention. The laser beam is controlled by means of a predetermined programmed line and/or scanning movement.

Irradiation with electron beams is a further possibility of differentiation. Electron beams can thoroughly decompose and crosslink mixtures which comprise one of the compounds according to the invention and a compound which can be split by acid, and also many other organic materials, so that a negative image is produced when the nonirradiated portions are removed by solvents or exposure without an original, and developing.

At a lower intensity and/or a higher writing speed of the electron beam, however, the electron beam effects a differentiation in the direction of higher solubility, that is to say the irradiated layer portions can be removed by the developer. The most advantageous conditions can readily be established by preliminary experiments.

The radiation-sensitive mixtures comprising one of the compounds according to the invention are preferably used in the production of printing forms, that is to say in particular offset printing forms, halftone gravure printing forms and screen-printing forms, in photoresist solutions and in so-called dry resists.

The examples which follow serve to explain the invention in more detail; the preparation of various compounds according to the invention is described first, and this is followed by the use of some of these compounds in radiation-sensitive mixtures.

In the examples, parts by weight (pbw) and parts by volume (pbv) have the same relationship as the g and the ml. Unless otherwise stated, percentage data and quantitative data are to be understood as weight units.

TABLE I

Compounds of the formula I with $Q = S$; $R^1 =$ Benzene ring

| Compound No. | R | M | L | n | $(CX_3)_m$ |
|---|---|---|---|---|---|
| 1 | $C_2H_5$ | 1,2-Phenylene | H | 1 | 4-$CCl_3$ |
| 1a | $C_2H_5$ | 5-$CH_3$-1,2-Phenylene | H | 1 | 4-$CCl_3$ |
| 1b | $CH_2C_6H_5$ | 1,2-Phenylene | H | 1 | 4-$CCl_3$ |
| 2 | $C_2H_5$ | 1,2-Phenylene | RX | 1 | 4-$CCl_3$ |
| 3 | $C_2H_5$ | 1,2-Phenylene | H | 1 | 3-$CCl_3$ |
| 4 | $CH_3$ | 1,2-Phenylene | H | 1 | 4-$CCl_3$ |
| 5(V) | $C_2H_5$ | 1,2-Phenylene | H | 1 | 4-$CF_3$ |
| 6 | $C_2H_5$ | 1,2-Phenylene | H | 0 | $CCl_3$ |
| 6a | $CH_3$ | 1,2-Phenylene | H | 0 | $CCl_3$ |
| 6b | $C_2H_5$ | 5-$CH_3$-1,2-Phenylene | H | 0 | $CCl_3$ |
| 6c | $CH_2C_6H_5$ | 1,2-Phenylene | H | 0 | $CCl_3$ |
| 7 | $C_2H_5$ | 1,2-Phenylene | H | 1 | 3,5-$(CCl_3)_2$ |
| 8 | $C_2H_4OCH_3$ | 1,2-Phenylene | H | 1 | 4-$CCl_3$ |
| 8a | $(CH_2)_5CH_3$ | 1,2-Phenylene | H | 1 | 4-$CCl_3$ |

TABLE I-continued

Compounds of the formula I with $Q = S$; $R^1 =$ Benzene ring

| Compound No. | R | M | L | n | $(CX_3)_m$ |
|---|---|---|---|---|---|
| 9(V) | $C_2H_5$ | 1,2-Phenylene | H | 1 | — |

(V) = Comparison compound
Ph = Phenylene
RX = CO—Ph—$CCl_3$(p)

TABLE II

Compounds of the formula I with $Q = S$; $M = $ 1,2-Naphthylene $R = CH_3$

| Compound No. | $R^1$ | L | n | $(CX_3)_m$ |
|---|---|---|---|---|
| 10 | 1,4-Phenylene | H | 1 | $CCl_3$ |
| 10a | 1,3,5-Phentriyl | H | 1 | $(CCl_3)_2$ |
| 11(V) | 1,4-Phenylene | H | 1 | $CF_3$ |
| 12(V) | Furyl-(2) | Furyl-(2)-carbonyl | 1 | — |
| 13 | — | H | 0 | $CCl_3$ |
| 14(V) | Phenyl | H | 1 | — |

TABLE III

Compounds of the formula I with $Q = C(CH_3)_2$; $L = H$; $X = Cl$; $R = CH_3$

| Compound No. | M | $R^1$ | n | m |
|---|---|---|---|---|
| 15 | 1,2-Phenylene | 1,4-Phenylene | 1 | 1 |
| 15a | 5-Cl-1,2-Phenylene | 1,4-Phenylene | 1 | 1 |
| 15b | 1,2-Phenylene | 1,3-Phenylene | 1 | 1 |
| 16 | 1,2-Phenylene | — | 0 | 1 |
| 16a | 5-Cl-1,2-Phenylene | — | 0 | 1 |
| 17 | 1,2-Phenylene | 1,3,5-Phentriyl | 1 | 2 |

TABLE IV

Compounds of the formula I with $Q = S$; $L = H$; $X = Cl$; $R^1 =$ 1,4-Phenylene; $R = C_2H_5$

| Compound No. | M | n |
|---|---|---|
| 18 | $C_2H_5OCO-C-$ <br> $\parallel$ <br> $CH_3-C-$ | 1 |
| 19 | $C_2H_5OCO-C-$ <br> $\parallel$ <br> $CH_3-C-$ | 0 |
| 20 | Phenyl-C— <br> $\parallel$ <br> Phenyl-C— | 1 |
| 20a | Phenyl-C— <br> $\parallel$ <br> H—C— | 1 |
| 21 | Phenyl-C— <br> $\parallel$ <br> Phenyl-C— | 0 |
| 21a | Phenyl-C— <br> $\parallel$ <br> H—C— | 0 |

TABLE V

Compounds of the formula I with $Q =$ Ethen-1,2-ylene; $M = $ 1,2-Phenylene $R = CH_3$; $n = O$; $X = Cl$

| | L |
|---|---|
| 22 | H |

TABLE V-continued

Compounds of the formula I with
Q = Ethen-1,2-ylene;M= 1,2-Phenylene R = CH₃; n = O;
X = Cl

| | L |
|---|---|
| 23 | Trichloroacetyl |

TABLE VI

Compounds of the formula I with
Q = Se; L = H; X = Cl; $R^1$ = 1,4-Phenylene; R = $C_2H_5$; m = 1

| Compound No. | M | n |
|---|---|---|
| 24 | 1,2-Phenylene | 1 |
| 25 | 5-CH₃-1,2-Phenylene | 1 |
| 26 | 5-CH₃O-1,2-Phenylene | 1 |
| 27 | 1,2-Phenylene | 0 |

PREPARATION EXAMPLE 1

Preparation of compound 1

(A) 3-ethyl-2-methyl-benzothiazolium p-toluenesulfonate 300 g (2 mol) of 2-methylbenzothiazole and 440 g (2.2 mol) of ethyl p-toluenesulfonate (or a mixture of ethyl o- and p-toluenesulfonate) are heated with stirring to 150° C., the temperature rising to about 200° C. due to the exothermic reaction. After 10 minutes, the mixture is poured into two liters of acetone, and the product which has precipitated is filtered off with suction, washed with acetone and dried in vacuo. Yield 730 g (98%).

(B) 2-(p-trichloromethylbenzoylmethylene)-3-ethyl-benzothiazoline (compound 1).

35 g (0.1 mol) of 3-ethyl-2-methyl-benzothiazolium p-toluenesulfonate are suspended in 300 ml of toluene, 28 g (0.11 mol) of p-trichloromethyl-benzoyl chloride are added, and 23 g (0.23 mol; 31.5 ml) of triethylamine are added dropwise at 15° C.

After 3-4 hours at room temperature, the product which has precipitated is filtered off will suction and washed with a small amount of methanol.

The product is recrystallized from ethanol, ethyl acetate, acetone or acetonitrile.

Yield: 34 g (85%).
Melting point: 174°-176° C.
$C_{18}H_{14}Cl_3NOS$: calc.: C 54.22; H 3.54; N 3.51; Cl 26.67.
MW: 398.74 found: C 54.2; H 3.4; N 3.5; Cl 26.4.
UV in dimethylformamide (DMF): 396 nm (30,900)

The following are prepared analogously

Compound 1a:
2-(p-trichloromethyl-benzoylmethylene)-3-ethyl-5-methyl-benzothiazoline Melting point: 181°-183° C.
$C_{19}H_{16}Cl_3NOS$: calc: C 55.29; H 3.91; N 3.39; Cl 25.77.
MW: 412.77 found: C 55.0; H 4.0; N 3.3; Cl 25.6.
UV (in DMF): 398 nm (32,800).

Compound 1b:
2-(p-trifluoromethyl-benzoylmethylene)-3-benzyl-benzothiazoline Melting point: 182°-185° C.
$C_{23}H_{16}Cl_3NOS$: calc.: C 59.95; H 3.50; N 3.04; Cl 23.68.
MW: 460.81 found: C 59.8; H 3.5; N 3.0; Cl 23.0.
UV (in DMF): 395 nm (31,500).

Compound 3:
2-(m-trichloromethyl-benzoylmethylene)-3-ethyl-benzothiazoline

Melting point: 157°-159° C.
$C_{18}H_{14}Cl_3NOS$: calc: C 54.22; H 3.54; N 3.51; Cl 26.67.
MW: 398.74 found: C 54.3; H 3.6; N 3.5; Cl 26.4.
UV (in DMF): 388 nm (46,900).

Compound 4:
2-(p-trichloromethyl-benzoylmethylene)-3-methyl-benzothiazoline (from 2,3-dimethylbenzothiazolium p-toluenesulfonate)

Melting point: 194°-196° C.
$C_{17}H_{12}Cl_3NOS$: calc.: C 53.08; H 3.14; N 3.64; Cl 27.65.
MW: 384.71 found: C 54.0; H 3.4; N 3.6; Cl 27.2.
UV (in DMF): 295 nm (32,200).

Compound 5: (Comparison compound)
2-(p-trifluoromethylbenzoylmethylene)-3-ethyl-benzothiazoline Melting point: 179°-180° C.
$C_{18}H_{14}F_3NOS$ calc.: C 61.88; H 4.04; N 4.01.
MW: 349.37 found: C 62.1; H 4.1; N 4.1.
UV (in DMF): 392 nm (31,300).

Compound 6a:
2-(trichloroacetylmethylene)-3-methylbenzothiazoline

Melting point: 189°-190° C.
$C_{11}H_8Cl_3NOS$ calc: C 42.81; H 2.61; N 4.45; Cl 34.46.
MW: 308.62 found: C 42.5; H 2.5; N 4.3; Cl 34.5.
UV (in DMF): 369 nm (28,700).

Compound 7:
2-[3,5-bis-(trichloromethyl)-benzoylmethylene]-3-ethyl-benzothiazoline Melting point: 180°-183° C.
$C_{19}H_{13}Cl_6NOS$: calc.: C 44.22; H 2.54; N 2.71; Cl 41.22.
MW: 516.10 found: C 44.2; H 2.4; N 2.7; Cl 40.6.
UV (in DMF): 399 nm (30,700).

Compound 8:
2-(p-trichloromethyl-benzoylmethylene)-3-(2-methoxyethyl)-benzothiazoline (from 2-methyl-3-(2-methoxyethyl)-benzothiazolium p-toluenesulfonate)

Melting point: 162°-165° C.
$C_{19}H_{16}Cl_3NO_2S$: calc.: C 53.22; H 3.76; N 3.27; Cl 24.81.
MW: 428.77 found: C 53.4; H 3.9; N 3.2; Cl 24.9.
UV (in DMF): 396 nm (31,000).

Compound 8a:
2-(p-trichloromethyl-benzoylmethylene)-3-n-hexyl-benzothiazoline Melting point: 111°-113° C.
$C_{22}H_{22}Cl_3NOS$: calc.: C 58.10; H 4.88; N 3.08; Cl 23.38.
MW: 454.85 found: C 58.4; H 4.9; N 3.0; Cl 23.1.
UV (in DMF): 397 nm (32,100).

Compound 9: (Comparison compound)
2-benzoylmethylene-3-ethyl-benzothiazoline

Melting point: 139°–140° C.
$C_{17}H_{15}NOS$: calc.: C 72.57; H 5.37; N 4.98.
MW: 281.38 found: C 72.6; H 5.6; N 5.0.
UV (in DMF): 381 nm (36,600).

Compound 10:
2-(p-trichloromethyl-benzoylmethylene)-3-methyl-naphtho[1,2-d]thiazoline (from 2,3-dimethyl-naphtho[1,2-d]thiazolium p-toluenesulfonate)

Melting point: 239°–242° C.
$C_{21}H_{14}Cl_3NOS$: calc.: C 58.01; H 3.25; N 3.22; Cl 24.46.
MW: 434.77 found: C 57.7; H 3.3; N 2.9; Cl 24.3.
UV (in DMF): 412 nm (35,200).

Compound 10a:
2-(3,5-bis-trichloromethyl-benzoylmethylene)-3-methyl-naphtho[1,2-d]thiazoline Melting point: 241°–242° C.
$C_{22}H_{13}Cl_6NOS$: calc.: C 47.86; H 2.37; N 2.54; Cl 38.53.
MW: 552.14 found: C 47.6; H 2.3; N 2.2; Cl 38.5.
UV (in DMF): 415 nm (33,400).

Compound 11: (Comparison compound)
2-(p-Trifluoromethyl-benzoylmethylene)-3-methyl-naphtho[1,2-d]thiazoline (from 2,3-dimethyl-naphtho[1,2-d]thiazolium p-toluenesulfonate)

Melting point: 252°–254° C.
$C_{21}H_{14}F_3NOS$: calc.: C 65.45; H 3.66; N 3.63.
MW: 385.41 found: C 64.7; H 3.8; N 3.6.
UV (in DMF): 409 nm (34,200).

Compound 13:
2-(trichloroacetylmethylene-3-methyl-naphtho[1,2-d]thiazoline (from 2,3-dimethyl-naphtho[1,2-d]thiazolium p-toluenesulfonate)

Melting point: 263° C.
$C_{15}H_{10}Cl_3NOS$: calc.: C 50.23; H 2.81; N 3.91; Cl 29.65.
MW: 358.67 found: C 50.2; H 2.9; N 3.9; Cl 30.2.
UV (in DMF): 387 nm (35,100).

Compound 14: (Comparison compound)
2-benzoylmethylene-3-methyl-naphtho[1,2-d]-thiazoline Melting point: 220°–222° C.
$C_{20}H_{15}NOS$: calc.: C 75.68; H 4.76; N 4.41.
MW: 317.41 found: C 75.4; H 4.8; N 3.9.
UV (in DMF): 331 nm (4,900), 399 nm (38,900).

Compound 24: 2-(p-trichloromethyl-benzoylmethylene)-3-ethyl-benzoselenazoline
Melting point: 175°–178° C.
$C_{18}H_{14}Cl_3NOS$: calc.: C 48.51; H 3.17; N 3.14; Cl 23.87.
MW: 445.77 found: C 48.3; H 3.2; N 3.1; Cl 23.6.
UV (in DMF): 399 nm (29,900).

Compound 25:
2-(p-trichloromethyl-benzoylmethylene)-3-ethyl-5-methyl-benzoselenazoline Melting point: 195°–197° C.

$C_{19}H_{16}Cl_3NOSe$: calc.: C 49.65; H 3.51; N 3.05; Cl 23.14.
MW: 459.66 found: C 49.9; H 3.7; N 3.1; Cl 23.0.
UV (in DMF): 401 nm (30,800).

Compound 26:
2-(p-trichloromethyl-benzoylmethylene)-3-ethyl-5-methoxy-benzoselenazoline Melting point: 174°–176° C.
$C_{19}H_{16}Cl_3NO_2Se$: calc.: C 47.98; H 3.39; N 2.94; Cl 22.36.
MW: 475.66 found: C 48.0; H 3.4; N 2.9; Cl 22.1.
UV (in DMF): 407 nm (30,100).

Compound 27:
2-trichloroacetylmethylene-3-ethyl-benzoselenazoline

Melting point: 139°–140° C.
$C_{12}H_{10}Cl_3NOSe$: calc.: C 39.00; H 2.73; N 3.79; Cl 28.78.
MW: 369.54 found: C 39.0; H 2.8; N 3.8; Cl 28.5.
UV (in DMF): 371 nm (29,500).

PREPARATION EXAMPLE 2

Preparation of compound 15:
2-(p-trichloromethyl-benzoylmethylene)-1,3,3-trimethylindoline 10.3 ml (16.6 g; 92 mmol) of trichloroacetyl chloride are added dropwise at 0°–5° C. to 13.48 g (80 mmol) of 1,3,3-trimethyl-2-methylene-indoline (tribase) and 26 ml (188 mmol) of triethylamine, dissolved in 300 ml of anhydrous toluene. The mixture is stirred for three hours at room temperature, the precipitate is filtered off, and the filtrate is washed with water, dried over sodium sulfate and concentrated. The product is recrystallized twice from diisopropyl ether.

Yield 12.6 g (49%).
Melting point: 170°–171° C.
$C_{20}H_{18}Cl_3NO$: calc.: C 60.86; H 4.60; N 3.55; Cl 26.94.
MW: 394.72 found: C 61.0; H 4.6; N 3.6; Cl 26.6.
UV (in DMF): 395 nm (26,300).

The following are prepared analogously

Compound 15a:
2-(p-trichloromethyl-benzoylmethylene)-1,3,3-trimethyl-5-chloro-indoline Melting point: 164°–171° C.
$C_{20}H_{17}Cl_4NO$: calc.: C 55.97; H 3.99; N 3.26; Cl 33.04.
MW: 429.18 found: C 55.6; H 3.9; N 3.2; Cl 33.2.
UV (in DMF): 394 nm (28,700).

Compound 15b:
2-(m-trichloromethyl-benzoylmethylene)-1,3,3-trimethyl-indoline

Melting point: 161°–165° C.
$C_{20}H_{18}Cl_3NO$: calc.: C 60.86; H 4.60; N 3.55; Cl 26.94.
MW: 394.72 found: C 61.1; H 4.6; N 3.6; Cl 26.8.
UV (in DMF): 388 nm (28,100).

Compound 16:
2-trichloroacetylmethylene-1,3,3-trimethylindoline

Melting point: 101° C.
$C_{14}H_{14}Cl_3NO$: calc.: C 52.77; H 4.43; N 4.40; Cl 33.38.
MQ: 318.63 found: C 53.1; H 4.4; N 4.4; Cl 33.1.

UV (in DMF): 375 nm (25,900).

Compound 16a:
2-trichloroacetylmethylene-1,3,3-trimethyl-5-chloro-indoline

Melting point: 163°–165° C.
$C_{14}H_{13}Cl_4NO$: calc.: C 47.63; H 3.71; N 3.97; Cl 40.16.
MW: 353.08 found: C 47.9; H 3.7; N 4.0; Cl 40.2.
UV (in DMF): 376 nm (28,000).

Compound 17:
2-[3,5-bis-(trichloromethyl)-benzoylmethylene]-1,3,3-trimethyl-indoline (from 2-methylene-1,3,3-trimethylindoline)

Melting point: 185°–186° C.
$C_{21}H_{17}Cl_6NO$: calc.: C 49.26; H 3.35; N 2.74; Cl 41.54.
MW: 512.09 found: C 49.6; H 3.6; N 2.6; Cl 40.9.
UV (in DMF): 398 nm (24,600).

PREPARATION EXAMPLE 3

Preparation of compound 2:
2-[bis-(p-trichloromethylbenzoyl)-methylene]-3-ethyl-benzothiazoline 12 g (46.5 mmol) of p-trichloromethyl-benzoyl chloride are added dropwise at 5°–15° C. to 7 g (20 mmol) of 2-methyl-3-ethylbenzothiazolium p-toluenesulfonate in 30 ml of dry pyridine. The mixture is heated at 100° C. for two hours. After cooling, the pyridine is distilled off in vacuo and 80 ml of methanol are added to the residue. The product which has precipitated is recrystallized from acetonitrile.

Yield: 7.5 g (60%).
Melting point: 205°–207° C.
$C_{26}H_{17}Cl_6NO_2S$: calc.: C 50.35; H 2.76; N 2.26; Cl 34.30.
MW: 620.21 found: C 50.6; H 3.0; N 2.3; Cl 34.4.
UV (in DMF): 372 nm (25,300).

The following is prepared analogously

Compound 12: (Comparison compound)
2-[bis-(2-furoyl)-methylene]-3-methyl-naphtho[1,2-d]thiazoline (from 2,3-dimethyl-naphtho[1,2-d]thiazolium p-toluenesulfonate)

Melting point: 205°–206° C.
$C_{23}H_{15}NO_4S$: calc.: C 68.82; H 3.77; N 3.49.
MW: 401.44 found: C 68.7; H 3.9; N 3.5.
UV (in DMF): 408 nm (35,000).

PREPARATION EXAMPLE 4

Preparation of compound 6:
2-trichloroacetylmethylene-3-ethyl-benzothiazoline 10 g (28.6 mmol) of 2-methyl-3-ethyl-benzothiazolium p-toluenesulfonate are suspended in 150 ml of toluene, 6.8 g (67.2 mmol) of triethylamine are added and, at 5°–10° C. 6 g (33 mmol) of trichloroacetyl chloride, dissolved in a minor amount of toluene, are added dropwise. After three hours at room temperature, the ammonium salts are filtered off with suction, and the reaction solution is washed with water, dried over sodium sulfate and concentrated in vacuo. The product is caused to crystallize from the diisopropyl ether.

Yield: 7.2 g (78%).
Melting point: 136°–139° C.
$C_{12}H_{10}Cl_3NOS$: calc.: C 44.67; H 3.12; N 4.34; Cl 32.97.
MW: 322.64 found: C 44.8; H 3.2; N 4.2; Cl 33.1.
UV (in DMF): 369 nm (31,600).

The following are prepared analogously

Compound 6b:
2-trichloroacetylmethylene-3-ethyl-5-methyl-benzothiazoline

Melting point: 199°–200° C.
$C_{13}H_{12}Cl_3NOS$: calc.: C 46.38; H 3.59; N 4.16; Cl 31.59.
MW: 336.67 found: C 46.4; H 3.7; N 4.0; Cl 31.3.
UV (in DMF): 370 nm (28,500).

Compound 6c:
2-trichloroacetylmethylene-3-benzylbenzothiazoline

Melting point: 197°–198° C.
$C_{17}H_{12}Cl_3NOS$: calc.: C 53.08; H 3.14; N 3.64; Cl 27.65.
MW: 384.71 found: C 53.2; H 3.2; N 3.6; Cl 27.5.
UV (in DMF): 369 nm (32,400).

PREPARATION EXAMPLE 5

Preparation of compound 18:
2-(p-trichloromethyl-benzoylmethylene)-3-ethyl-4-methyl-5-ethoxycarbonyl-thiazoline (A) 2,4-dimethyl-3-ethyl-5-ethoxycarbonyl-thiazolium p-toluenesulfonate Ethyl 2-chloro-acetoacetate is condensed with thioacetamide to 2,4-dimethyl-5-ethoxycarbonyl-thiazoline which is reacted, analogously to Preparation Example 1 A, with ethyl p-toluenesulfonate to give the p-toluenesulfonate of the quaternary ammonium base.

(B) Compound 18

Analogous to Preparation Example 1 B, the 2,4-dimethyl-3-ethyl-5-ethoxycarbonyl-thiazolium p-toluene-sulfonate is reacted with p-trichloromethylbenzoyl chloride to give 2-(p-trichloromethyl-benzoylmethylene)-3-ethyl-4-methyl-5-ethoxycarbonylthiazoline.

Melting point: 214°–216° C.
$C_{18}H_{18}Cl_3NO_3S$: calc.: C 49.73; H 4.17; N 3.22; Cl 24.46.
MW: 434.77 found: C 49.7; H 4.2; N 3.2; Cl 24.1.
UV (in DMF): 317 nm (5,300), 402 nm (29,300).

The following compounds are prepared analogously

Compound 19:
2-trichloroacetylmethylene-3-ethyl-4-methyl-5-ethoxycarbonyl-thiazoline Melting point: 144°–146° C.
$C_{12}H_{12}Cl_3NO_3S$: calc.: C 40.9; H 3.93; N 3.91; Cl 29.65.
MW: 358.67 found: C 40.0; H 3.9; N 3.7; Cl 29.6.
UV (in DMF): 295 nm (6,100), 376 nm (26,700).

Compound 20:
2-(p-trichloromethyl-benzoylmethylene-3-ethyl-4,5-diphenyl-thiazoline Melting point: 210°–211° C.
$C_{26}H_{20}Cl_3NOS$: calc.: C 62.35; H 4.02; N 2.80; Cl 21.23.
MW: 500.88 found: C 62.2; H 4.2; N 2.6; Cl 21.1.
UV (in DMF): 322 nm (5,900), 412 nm (27,400).

Compound 20a:
2-(p-trichloromethyl-benzoylmethylene)-3-ethyl-5-phenyl-thiazoline Melting point: 172°–175° C.
$C_{20}H_{16}Cl_3NOS$: calc.: C 56.55; H 3.80; N 3.30; Cl 25.04.
MW: 424.78 found: C 56.2; H 3.7; N 3.1; Cl 24.8.
UV (in DMF): 399 nm (22,700).

Compound 21:
2-trichloroacetylmethylene-3-ethyl-4,5-diphenyl-thiazoline

Melting point: 161°–162° C.
$C_{20}H_{16}Cl_2NOS$ calc.: C 56.55; H 3.80; N 3.30; Cl 25.04.
MW: 424.78 found: C 56.8; H 3.8; N 3.2; Cl 24.8.
UV (in DMF): 292 nm (S, 7,200), 380 nm (25,800).

Compound 21a:
2-trichloroacetylmethylene-3-ethyl-5-phenyl-thiazoline

Melting point: 144°–145° C.
$C_{14}H_{12}Cl_3NOS$: calc.: C 48.23; H 3.47; N 4.02; Cl 30.50.
MW: 348.68 found: C 48.1; H 3.7; N 4.0; Cl 30.2.
UV (in DMF): 366 nm (24,400).

PREPARATION EXAMPLE 6

Preparation of compounds 22 and 23

(A) 1,2-dimethyl-quinolinium p-toluenesulfonate:

71.5 g (0.5 mol) of quinaldine and 102.3 g (0.55 mol) of methyl p-toluenesulfonate are heated to 100° C. within about 10 minutes. The exothermic reaction which starts raises the temperature of the reaction mixture to 180° C. After 10 minutes, the mixture is poured onto acetone and filtered with suction, and the residue is washed with acetone and dried.

Yield: 151 g (0.46 mol=92%).

(B) 2-trichloroacetylmethylene-1-methyl-1,2-dihydroquinoline and 2-(bis-trichloroacetyl-methylene)-1-methyl-1,2-dihydroquinoline.

6 g (33 mmol) of trichloroacetyl chloride are added dropwise at 0°–5° C. to 10 g (30 mmol) of 1,2-dimethyl-quinolinium p-toluenesulfonate in 25 ml of pyridine. After 2 hours at room temperature, methylene chloride is added, and the solution is washed with water, dried over sodium sulfate, concentrated and chromatographed twice with cyclohexane/ethyl acetate (1:1) on silica gel.

1st. eluted zone: 300 mg.

Compound 22:
2-trichloroacetyl-1-methyl-1,2-dihydroquinoline

Melting point: 228°–230° C.
$C_{13}H_{10}Cl_3NO$ calc.: C 51.60; H 3.33; N 4.63; Cl 35.15.
MW: 302.59 found: C 51.6; H 3.3; N 4.4; Cl 35.1.
UV (in DMF): 305 nm (12,500), 402 nm (S, 21,200), 419 nm (30,200), 441 nm (23,700).

2nd. eluted zone: 200 mg.

Compound 23:
2-(bis-trichloroacetyl-methylene)-1-methyl-1,2-dihydroquinoline

Melting points: 175°–176° C.
$C_{15}H_9Cl_6NO_2$ calc.: C 40.22; H 2.03; N 3.13; Cl 47.49.
MW: 447.96 found: C 40.1; H 2.0; N 2.7; Cl 46.8.
UV (in DMF): 323 nm (13,900), 442 nm (7,100).

APPLICATION EXAMPLE 1

A mechanically roughened aluminum plate is spin-coated with a solution of:
0.5 pbw of compound 1,
23.75 pbw of a polyacetal of triethylene glycol and 2-ethyl-butyraldehyde and
75.0 pbw of a cresol/formaldehyde novolak (melting range 105°–120° C. by the capillary method of DIN 53,181) in
24.25 pbw of 2-ethoxy-ethanol and
375 pbw of methyl ethyl ketone and is dried at 100° C.

The coated plate is exposed through a step wedge, in which the optical density of one step differs by a factor of $\sqrt{2}$ from the next step, and the positive image is developed with a solution of
5.5 pbw of sodium metasilicate . 9 $H_2O$,
3.4 pbw of trisodium phosphate . 12 $H_2O$,
0.4 pbw of sodium dihydrogen phosphate (anhydrous) and
90.7 pbw of desalinated water.

Table VII shows that the number of developed wedge steps increases by 2 in each case when the exposure time is doubled.

TABLE VII

| Exposure time (minutes) | Developed wedge steps |
|---|---|
| 0.5 | 3 |
| 1 | 5 |
| 2 | 7 |
| 4 | 9 |

APPLICATION EXAMPLE 2

This example shows that, among the compounds according to the invention, those with a p-trichloromethylbenzoyl group are particularly sensitive.

By contrast, the trifluoromethylbenzoylmethylene-thiazoles (compounds 5 and 11) known from U.S.A. Defense Publication T 900011-Q and the compounds without a trihalogenomethyl group, known from German Auslegeshrift No. 2,717,778, are ineffective.

The procedure followed is analogous to Application Example 1, compound 1 in the coating mixture being replaced by the same quantity of one of the compounds indicated in Table VIII.

TABLE VIII

| Compound No. | Wedge steps developed at an exposure time of | |
|---|---|---|
| | 2 minutes | 4 minutes |
| 1 | 7 | 9 |
| 1a | 5 | 7 |
| 1b | 5 | 8 |
| 2 | 1 | 3 |
| 3 | 0 | 1 |
| 4 | 7 | 9 |
| 6 | 5 | 8 |
| 6a | 5 | 7 |
| 6b | 5 | 7 |
| 6c | 5 | 8 |
| 7 | 0 | 1 |
| 8 | 6 | 8 |
| 8a | 5 | 8 |
| 10 | 6 | 8 |
| 10a | 0 | 2 |
| 13 | 5 | 7 |
| 15 | 5 | 7 |
| 15a | 4 | 5 |
| 15b | 0 | 0 |
| 16 | 2 | 4 |

TABLE VIII-continued

| Compound No. | Wedge steps developed at an exposure time of | |
|---|---|---|
| | 2 minutes | 4 minutes |
| 16a | 3 | 6 |
| 17 | 0 | 1 |
| 18 | 4 | 6 |
| 19 | 5 | 7 |
| 20 | 2 | 4 |
| 20a | 3 | 5 |
| 21 | 2 | 3 |
| 21a | 3 | 5 |
| 22 | 0 | 1 |
| 23 | 0 | 0 |
| 24 | 5 | 8 |
| 25 | 6 | 8 |
| 26 | 5 | 8 |
| 27 | 5 | 8 |

| Comparison compounds with CF$_3$ - group | Exposure time | |
|---|---|---|
| | 8 minutes | 16 minutes |
| 5 | 0 | 0 |
| 11 | 0 | 0 |
| Without CX$_3$ - group | Exposure time | |
| | 8 minutes | 16 minutes |
| 9 | 0 | 0 |
| 12 | 0 | 0 |
| 14 | 0 | 0 |
| With CCl$_3$ - group | Exposure time | |
| | 2 minutes | 4 minutes |
| A | 6 | 9 |
| B | 7 | 9 |
| C | 6 | 8 |

A = 2-(p-methoxyphenyl)-4-chloro-5-(p-trichloromethyl-phenyl)-oxazole
B = 2-(p-trichloromethylphenyl)-4-chloro-5-(p-methoxy-phenyl)-oxazole
C = 2,4-bis-(trichloromethyl)-6-(4-ethoxynaphth-1-yl)-s-triazine

APPLICATION EXAMPLE 3

An aluminum plate, mechanically roughened on one side by wire-brushing, was coated with the following solution:
3 pbw of the novolak indicated in Application Example 1,
1 pbw of a polymeric acetal of 2-ethylbutyraldehyde and hexane-1,6-diol,
0.001 pbw of crystal violet base and
0.02 pbw of compound 10 in
96 pbw of a solvent mixture of ethylene glycol monoethyl ether and butyl acetate (4:1).

The dried layer had a layer weight of 2 g/m$^2$. It was exposed under a positive original for 100 seconds with a 5 kW metal halide lamp at a distance of 140 cm, an image contrast being produced by brightening-up of the exposed areas. The latter were washed out with a solution of
2.67 pbw of sodium metasilicate . 9 H$_2$O,
1.71 pbw of trisodium phosphate . 12 H$_2$O and
0.17 pbw of monosidum phosphate (anhydrous) in
95.45 pbw of fully desalinated water.

The plate was then rinsed with water in the customary manner and made ready for printing by wiping with 1% phosphoric acid. A high-performance planographic printing plate was obtained.

APPLICATION EXAMPLE 4

A solution was prepared from
6.5 pbw of a terpolymer of n-hexyl methacrylate, methacrylic acid and styrene (60:30:10), having a mean molecular weight of about 35,000 and an acid number of 195,
3.2 pbw of polyethylene glycol-400 dimethacrylate,
0.1 pbw of compound 15 and
0.04 pbw of an azo dye, prepared by coupling of 2,4-dinitro-6-chloro-benzenediazonium salt with 2-methoxy-5-acetylamino-N-cyanoethyl-N hydroxyethyl-aniline in
25 pbw of methyl ethyl ketone and
3 pbw of ethanol.

A biaxially stretched and thermoset polyethylene terephthalate film having a thickness of 25 μm was spin-coated with this coating solution in such a way that, after drying at 100° C., a layer weight of 45 g/m$^2$ was obtained. The dry resist film thus obtained was laminated by means of a commercially available laminator at 120° C. to a phenoplast laminate plate laminated with a 35 μm thick copper foil, and the plate was exposed for 40 seconds under a printed circuit board original. After exposure, the polyester film was peeled off, and the unexposed layer areas were washed out within one minute with 1% soda solution in a spraying apparatus.

After rinsing with water and slight etching with 15% ammonium peroxydisulfate solution, electroplating was carried out on the bared areas successively in the bright copper bath and the "Norma" nickel bath from Messrs. Schloetter and the "Autronex XX" gold bath from Messrs. Blasberg in each case with the current densities and layer thicknesses recommended by the manufacturer. After removal of the resist stencil with 5% KOH solution at 40°-50° C. and etching away the base copper thus exposed with conventional etches, a good printed circuit board was obtained.

APPLICATION EXAMPLE 5

For producing a positive dry resist, the following solution was prepared.
64.75 pbw of methyl ethyl ketone,
21.2 pbw of the novolak described in Application Example 1,
10 pbw of the bis-(5-ethyl-5-methoxymethyl-1,3-dioxolan-2-yl) ether of 2-ethyl-2-methoxymethyl-1,3-propanediol,
3.8 pbw of polyethyl acrylate of low viscosity,
0.05 pbw of crystal violet base and
0.2 pbw of compound 4.

A biaxially stretched and thermoset, 25 μm thick polyester film, pretreated with trichloroacetic acid/polyvinyl alcohol solution, was coated with this solution analogously to Application Example 4, dried and laminated to both sides of a copper sheet. After cooling, peeling off the carrier film and brief further drying in a drying cabinet at 80° C., the coated sheet was exposed on both sides with a congruent pair of originals in the form of a pocket. As in Application Example 1, the exposed layer areas were then removed, in this case by spraying both sides with the developer. A 25 μm thick resist was exposed for 40 seconds and developed for 45 seconds; with 12 μm resist thickness, 25 seconds exposure and 25 seconds development were sufficient. With both resist thicknesses, the plates were etched, after rinsing off the residues of alkaline developer, on both sides with commercially available ferric chloride solution until they were cleanly etched through their thicknesses. The resulting chemically milled components can also be freed from the resist stencil by means of about 3% KOH or NaOH solution or acetone.

APPLICATION EXAMPLE 6

For producing a negative dry resist, a solution of the following composition:
68.5 pbw of methyl ethyl ketone
19 pbw of a copolymer of polymethyl methacrylate/-methacrylic acid (98.2), having a molecular weight of about 34,000,
12 pbw of trimethylolpropane triacrylate,
0.2 pbw of compound 1,
0.2 pbw of leuco-crystal violet and
0.1 pbw of malachite green is applied to a support film as in Application Example 4.

The resulting uniform photopolymerizable layer of a thickness of 38 μm was laminated to a laminate plate laminated with copper foil and then exposed for 20 seconds in the exposure apparatus indicated in Application Example 3. In this case, the light-sensitive trichloroemthylphenyl compound both initiates the photopolymerization and causes formation of the color of crystal violet from the leuco compound.

If, in place of compound 1, the corresponding trifluoromethyl compound 5 is used in the same way, there is no reaction in the exposed areas, not even with an extended exposure time. If, however, compound 1 is replaced by compound 2, a markedly lower light sensitivity is obtained. Whereas the continuous tone step wedge is covered up to stage 8 when compound 1 is used, the corresponding layer with compound 2 at the same exposure shows adequate coverage only up to stage 2, after 1 minute of spray developing. If compound 1 is replaced by comparison compound A (Application Example 2), no image is obtained.

A result similar to that with compound 1 as the initiator is obtained when the compound 2-(4-ethoxynathth-1-yl)-4,6-bis-trichloromethyl-s-triazine is used as a comparison. However, the storage stability of this resist, laminated to copper, is markedly poorer. This is clear from the accelerated storage test at 40° C. Whereas the material with the known trichloromethyltriazine as the initiator gives, after 8 days' storage and subsequent exposure and developing, a continuous tone step wedge which is shorter by 3 wedge steps, the wedge is shortened by only about one step when compound 1 is used under otherwise identical conditions. After the same storage, the unexposed material with the known initiator shows a clear blue coloration, while the latter is only slight in the case of the material according to the invention.

APPLICATION EXAMPLE 7

A support of electrolytically roughened and anodically oxidized aluminum was spin-coated with a solution of
3 pbw of the novolak indicated in Application Example 1,
1 pbw of a polymer acetal of 2-ethylbutyraldehyde and triethylene glycol,
0.002 pbw of crystal violet base and
0.6 pbw of compound 1 in
76 pbw of 2-ethoxy-ethane and
19.4 pbw of butyl acetate and dried. The layer weight was 2.5 g/m². The printing plate obtained was exposed as in Application Example 3 and developed with the solution indicated in Application Example 1.

APPLICATION EXAMPLE 8

A phenoplast laminate plate with a 35 μm thick laminated copper foil was whirler-coated with a solution of
19 pbw of a terpolymer of butyl methacrylate, methyl methacrylate and methacrylate acid (78:20:2, molecular weight about 100,000),
12 pbw of dipentaerythritol hexacrylate,
0.2 pbw of compound 13 and
0.2 pbw of leuco-crystal violet in
68.6 pbw of butanone in such a way that, after drying at 100° C., a layer of 25 μm thickness was obtained. The plate was exposed for 30 seconds in the exposure apparatus indicated in Application Example 3 and developed by spraying with trichloroethane. The circuit pattern was further processed in the customary manner by electroplating, decoating and etching of the base copper.

APPLICATION EXAMPLE 9

A biaxially stretched and thermoset polyethylene terephthalate film of 25 μm thickness was spin-coated with a solution of
6.5 pbw of the terpolymer described in Application Example 4,
2.8 pbw of a polymerizable diurethane obtained by reacting 1 mol of 2,2,4-trimethyl-hexamethylene diisocyanate with 2 mol of hydroxyethyl methacrylate,
2.8 pbw of a polymerizable polyurethane prepared by reaction of 11 mol of 2,2,4-trimethylhexamethylene diisocyanate with 10 mol of anhydrous triethylene glycol and further reaction of the reaction product with 2 mol of hydroxyethyl methacrylate,
0.2 pbw of compound 4,
0.1 pbw of 3-mercapto-propionic acid 2,4-dichloroanilide,
0.035 pbw of the blue azo dye indicated in Application Example 4 and
2.8 pbw of the ester of 2,6-dihydroxy-benzoic acid with diethylene glycol mono-2-ethylhexyl ether in
35 pbw of methyl ethyl ketone and
2 pbw of ethanol in such a way that, after drying at 100° C., a layer weight of 28 g/m² was obtained.

The dry resist film obtained was laminated by means of a commercially available laminator at 120° C. to a phenoplast laminate plate laminated with a 35 μm thick copper foil. The plate was exposed for 20 seconds by means of a commercially available exposure apparatus. The original used was a line original with line widths and spacings down to 80 μm.

After exposure, the polyester film was peeled off, and the layer was developed for 50 seconds in a 0.8% Na₂CO₃ solution in spray developing apparatus.

The plate was then rinsed for 30 seconds with tap water, slightly etched for one minute in a 25% ammonium peroxydisulfate solution and then electroplated successively in the following electrolyte baths:

1. 40 minutes in a copper electrolyte bath from Messrs. Blasberg, Solingen, "Feinkornkupfer plastic-Bad" [Fine-grain copper plastic bath],
   Current density: 2 A/dm²
   Metal deposit: about 20 μm
2. 10 minutes in the nickel bath described in Application Example 4,
   Current density: 4 A/dm²
   Metal deposit: 6 μm, and
3. 15 minutes in an "Autronex N" type gold bath from Messrs. Blasberg, Solingen, Current density: 0.6 A/dm$^2$ Metal deposit: 2.5 μm.

The plate does not show any undercuttings or damage whatsoever.

The plate can then be decoated in 5% KOH solution at 50° C., and the bared copper can be etched away in the customary etching media.

What is claimed is:

1. A compound of the formula I

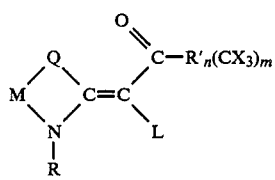

wherein

L represents a hydrogen atom or a substituent of the formula CO—RI(CX$_3$)$_m$,

M represents a substituted or unsubstituted alkylene radical or alkenylene radical or a 1,2-arylene radical, Q represents a sulfur, selenium or oxygen atom, a dialkylmethylene group, an alken-1,2-ylene radical, a 1,2-phenylene radical or an N-R group, whereby M+Q together form 3 or 4 ring members, R represents an alkyl, aralkyl or alkoxyalkyl radical, R$^1$ is a carbocyclic aromatic or heterocyclic aromatic group, and X is a chlorine, bromine or iodine atom, and m=1 or 2.

2. A compound as claimed in claim 1, wherein X represents a chlorine atom.

3. A compound as claimed in claim 1, wherein R$^1$ represents a phenylene or phentriyl radical.

4. A compound as claimed in claim 1, wherein Q represents a sulfur atom.

5. A light-sensitive mixture, comprising a compound (a) which includes a light-sensitive, heterocyclic organic compound as claimed in claim 1, and has at least one trihalogenomethyl substituent; and a compound (b) capable of reacting with the photoreaction product of said compound (a) to form a product having a light absorption or solubility in a developer different from that of compound (b).

6. The light-sensitive mixture as claimed in claim 5, wherein said compound (b) comprises an ethylenically unsaturated compound capable of undergoing free radical-initiated polymerization.

7. The light-sensitive mixture as claimed in claim 5, wherein said compound (b) comprises at least one C—O—C bond capable of being split by acid.

8. The light-sensitive mixture as claimed in claim 5, wherein said compound (b) is cationically polymerizable by an acid.

9. The light-sensitive mixture as claimed in claim 5, wherein said compound (b) can be crosslinked by acid.

10. The light-sensitive mixture as claimed in claim 5, wherein said compound (b) changes its color shade under the action of acid.

11. The light-sensitive mixture as claimed in claim 5, wherein compound (a) comprises from about 0.1 to 15% by weight, relative to its nonvolatile constituents of the mixture.

12. The light-sensitive mixture as claimed in claim 5, further comprising a water-insoluble polymeric binder.

13. The light-sensitive mixture as claimed in claim 12, wherein said binder is soluble in aqueous-alkaline solutions.

* * * * *

UNITED STATES PATENT AND TRADEMARK OFFICE
CERTIFICATE OF CORRECTION

PATENT NO. : 4,966,828

DATED : October 30, 1990

INVENTOR(S) : Reinhard Doenges et al

It is certified that error appears in the above-identified patent and that said Letters Patent is hereby corrected as shown below:

Column 23;

Claim 1, formula I, "$R'_n$" should read -- $R^1$ --.

Signed and Sealed this

Twenty-ninth Day of September, 1992

Attest:

DOUGLAS B. COMER

*Attesting Officer*   *Acting Commissioner of Patents and Trademarks*

UNITED STATES PATENT AND TRADEMARK OFFICE
CERTIFICATE OF CORRECTION

PATENT NO. : 4,966,828

DATED : October 30, 1990

INVENTOR(S) : Reinhard Doenges et al

It is certified that error appears in the above-identified patent and that said Letters Patent is hereby corrected as shown below:

Column 23, Claim 1, line 22, change RI to -- $R^1$ --.

Signed and Sealed this

Fifteenth Day of December, 1992

*Attest:*

DOUGLAS B. COMER

*Attesting Officer*      *Acting Commissioner of Patents and Trademarks*